United States Patent [19]
Henrikson

[11] Patent Number: 5,911,577
[45] Date of Patent: Jun. 15, 1999

[54] DISPOSABLE PROPHY ANGLE

[75] Inventor: Steven Ross Henrikson, Morristown, Tenn.

[73] Assignee: Team Technologies, Inc., Morristown, Tenn.

[21] Appl. No.: 09/169,386

[22] Filed: Oct. 9, 1998

[51] Int. Cl.$^6$ ...................................................... A61C 3/06
[52] U.S. Cl. .......................................... 433/125; 433/126
[58] Field of Search .................................... 433/118, 125, 433/126, 166

[56] References Cited

U.S. PATENT DOCUMENTS

| | | | |
|---|---|---|---|
| 3,472,045 | 10/1969 | Nelsen et al. ................................. | 64/4 |
| 3,727,313 | 4/1973 | Graham ......................................... | 32/27 |
| 4,842,516 | 6/1989 | Choisser ...................................... | 433/132 |
| 5,160,263 | 11/1992 | Meller et al. ............................. | 433/125 |
| 5,219,285 | 6/1993 | Meller et al. ............................. | 433/126 |
| 5,340,310 | 8/1994 | Bifulk ......................................... | 433/123 |
| 5,352,119 | 10/1994 | Sakurai ....................................... | 433/125 |
| 5,374,189 | 12/1994 | Mendoza ...................................... | 433/125 |
| 5,433,605 | 7/1995 | Strobl, Jr. .................................. | 433/112 |
| 5,496,218 | 3/1996 | Brahler .................................. | 433/125 X |
| 5,529,495 | 6/1996 | Edwards ................................. | 433/125 X |
| 5,571,012 | 11/1996 | Witherby et al. ........................ | 433/125 |
| 5,645,426 | 7/1997 | Grim et al. .............................. | 433/125 |
| 5,667,383 | 9/1997 | Mendoza et al. ......................... | 433/132 |
| 5,692,901 | 12/1997 | Roth et al. ................................ | 433/85 |

FOREIGN PATENT DOCUMENTS

| | | | |
|---|---|---|---|
| 06105853 | 4/1994 | Japan ................................. | A61C 1/08 |
| 06327699 | 11/1994 | Japan ................................. | A61C 3/02 |

*Primary Examiner*—Nicholas D. Lucchesi
*Attorney, Agent, or Firm*—Luedeka, Neely & Graham, P.C.

[57] ABSTRACT

A prophy angle dental tool comprises a disposable attachment to an air turbine type of dental tool drive motor. The disposable attachment has a single section tubular body that extends from a direct drive coupling with the drive motor power shaft housing to the driven dental implement. A quick-coupling hub at one end of a medial drive shaft receives a lug drive mechanism in the motor drive shaft. Externally, the coupling hub is confined to coaxial rotation within the motor shaft housing. The medial drive shaft extends unrestrained from the motor coupling hub along an internal void within the tubular body into geared engagement with a short shaft. The short shaft is rotatively driven about an axis that is substantially transverse of the tubular body length. A pinion gear on the inner end of the short shaft is engaged by a gear at the end of the medial drive shaft thereby driving the short shaft while simultaneously holding the short shaft within a short shaft housing bore.

15 Claims, 3 Drawing Sheets

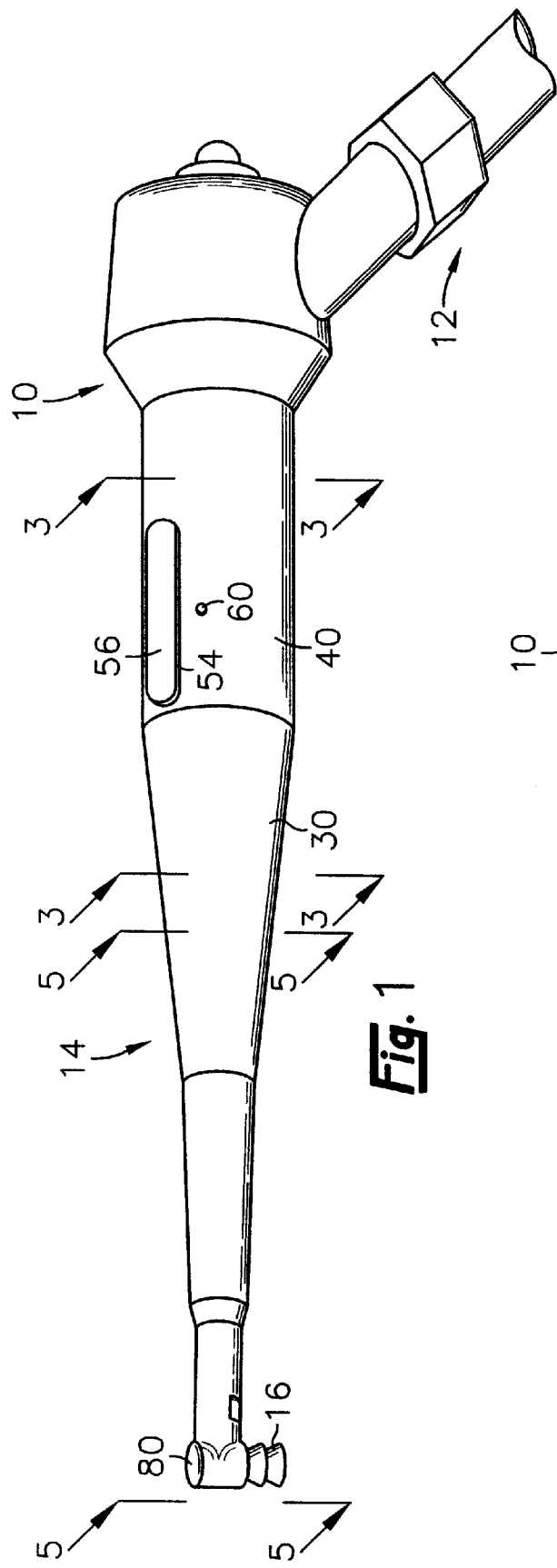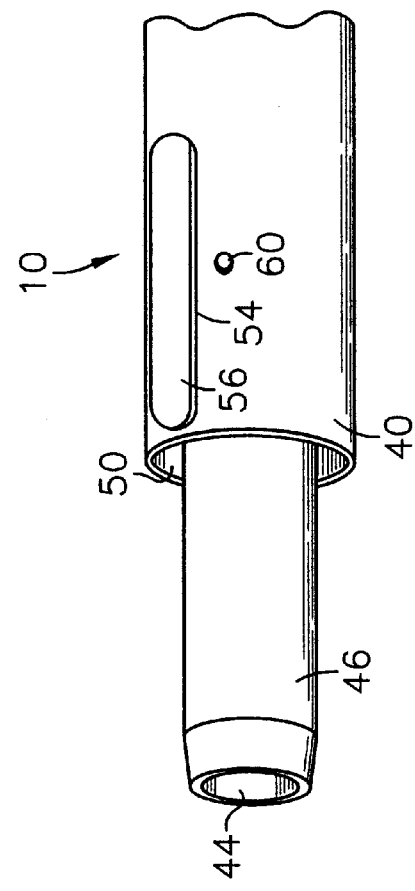
Fig. 1
Fig. 2

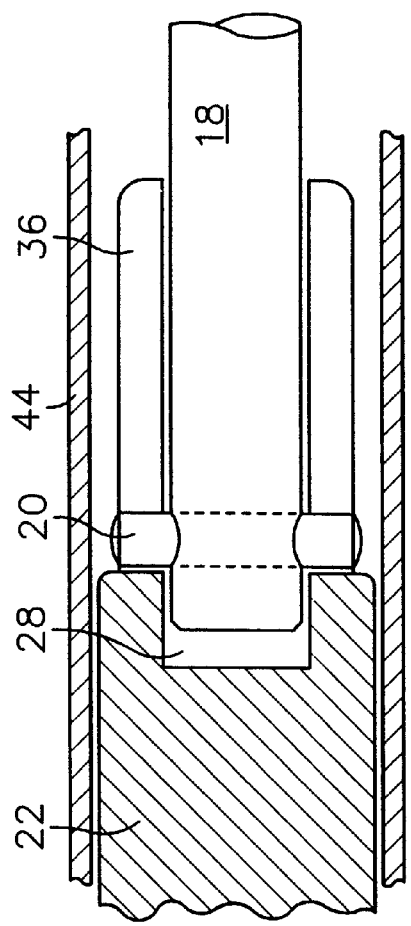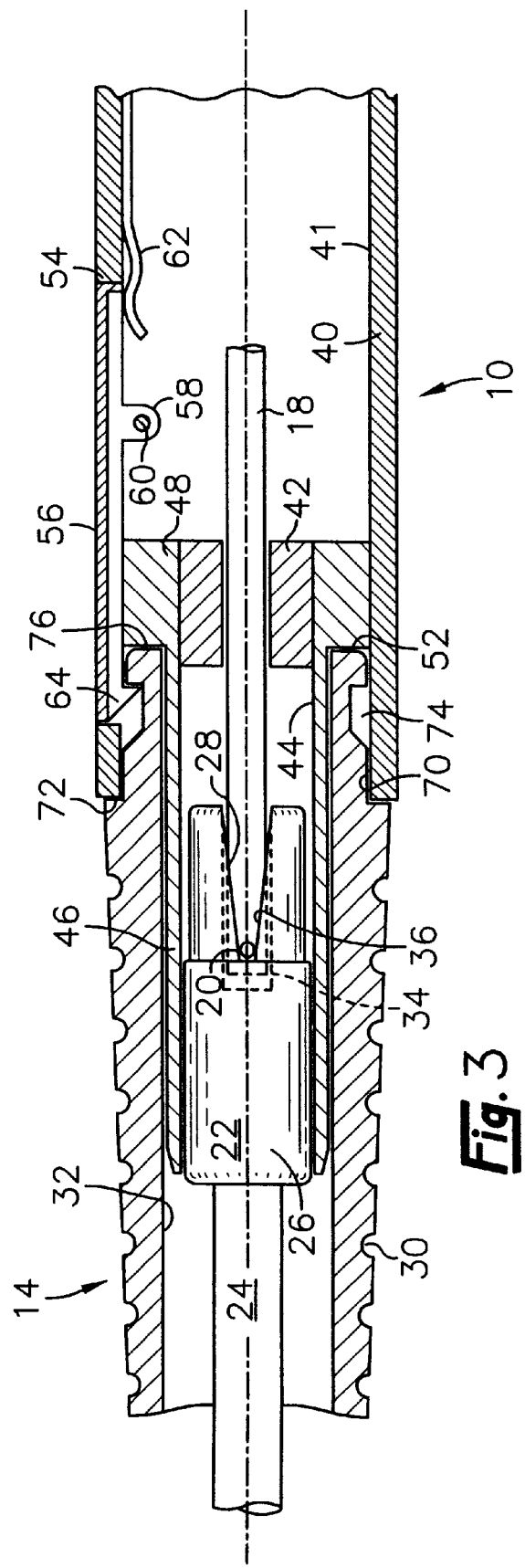

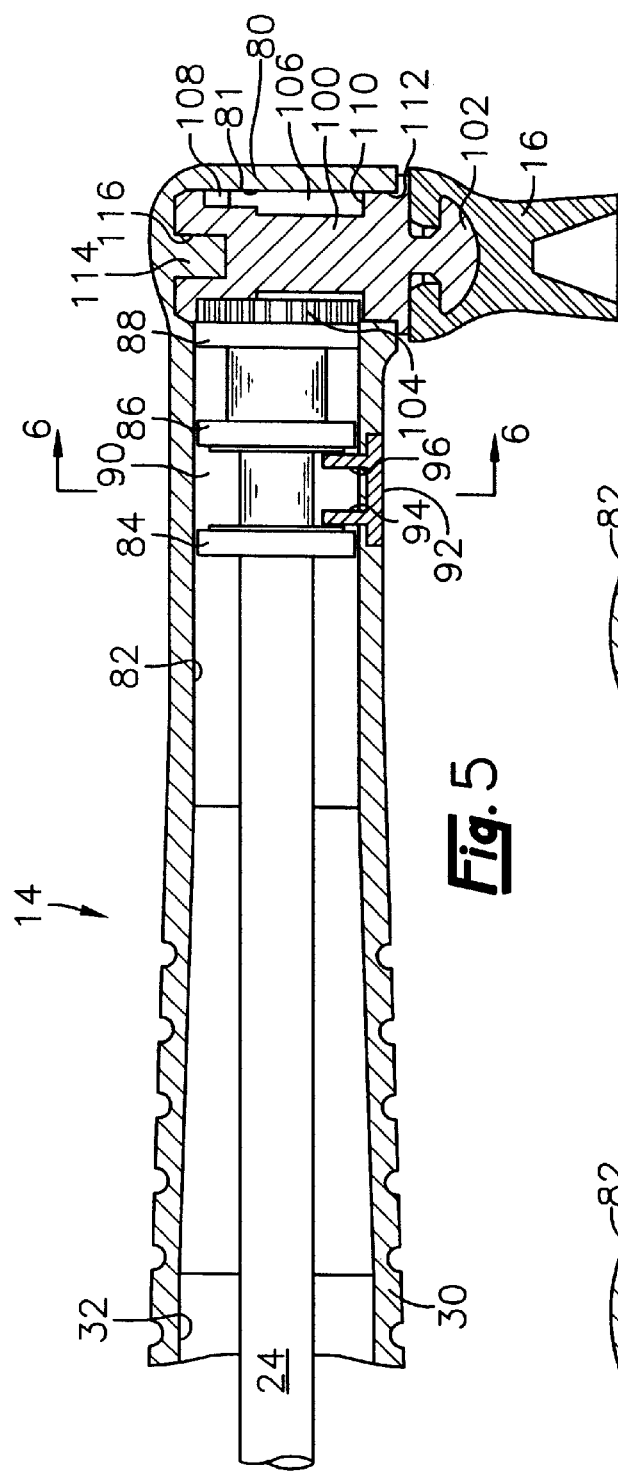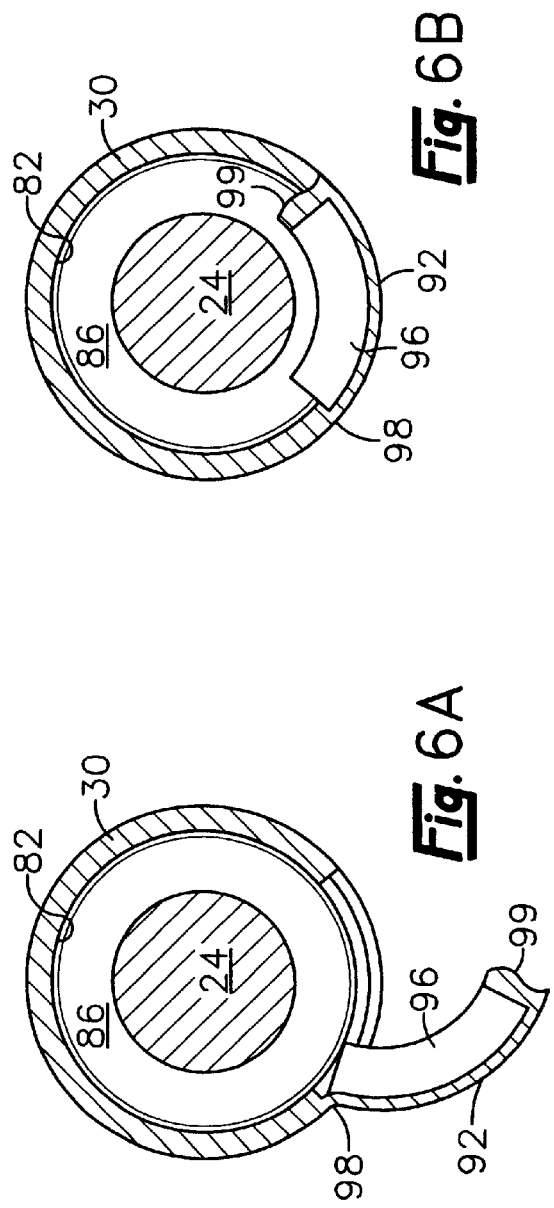

DISPOSABLE PROPHY ANGLE

BACKGROUND OF THE INVENTION

The present invention relates to a dental hand tool and more particularly, to a dental prophy angle for cleaning and polishing teeth.

Prophy angle is a term of art given to a small, rotary powered hand tool used uniquely by the dental profession for cleaning and polishing teeth. As originally constructed, the prophy angle comprised an integrated combination of an air turbine motor for directly driving a single, elongated drive shaft. The entire construction was of either die cast aluminum or machined stainless steel.

The drive shaft length was confined within a tubular housing that served as the tool handle. The length of the tool handle and hence the length of the drive shaft, was and is dictated by user convenience and manipulation facility. This is generally considered to be about 4 to 6 inches. The turbine rotor vane elements were secured to one end of a stainless steel drive shaft and an angle drive transmission gear on the other shaft end. The drive shaft gear teeth meshed with the pinion gear teeth of a short shaft that was confined to rotation about an axis aligned substantially normally to the drive shaft axis. A projected end of the short shaft included an implement spindle to which a brush or polishing head, for example, was selectively attached.

Prudent medical practice requires that all dental tools used in intimate proximity of a single patient be sterilized before reuse on another patient. Normal dental office sterilization processes include the use of a superheated steam autoclave. Construction parameters for dental tool turbines, however, require that they be extremely small and light. These characteristics dictate small and extremely fragile turbine vanes and radar bearings. As a further consequence of miniaturization, the cost of such turbines is relatively great.

Due to the fragile construction, repeated autoclave exposure rapidly accelerates the decline and failure of dental tool motors. This fact and the relatively high cost of the turbines has inspired further innovations to the tool type. Such further innovations include a segmented drive line whereby the turbine motor is separable from the handle or gripping tube that carries the drive shaft. Further, the gripping tube is separable from the implement spindle head. In this configuration, it is unnecessary to autoclave the turbine motor. Only the gripping tube segment and the spindle head need to be sterized after use.

As a still further innovation, the spindle head has been fabricated with injection molded plastic components with such economy that a spindle head is discarded after a single use. Hence, only the gripping tube segment of the tool assembly remains for autoclave sterilization. Unfortuantely, disposeability of the spindle head has widely induced an unsafe disposition among some dental care practitioners that the gripping tube need not be sterilized.

An additional objection to a segmented driveline for dental tools is the tendency for such designs to produce a greater degree of vibration at high rotational speeds near 5,000 rpm due to the intermediate driveline mass that is located at the coupling between the spindle head and the motor coupling.

One object of the present invention, therefore, is the provision of a disposable prophy angle attachment.

Another object of the invention is a disposable prophy angle attachment having sufficient length to require only a single drive shaft coupling between a dental tool motor and the prophy angle implement.

A further object of the invention is an elongated prophy angle attachment having low medial shaft vibration.

Also an object of the invention is a unitary prophy angle attachment having a minimum of only four functional components, each of which are formed by extrusion molded plastic and are collectively assembled with such simplicity as to economically justify disposal after a single use.

An additional object of the invention is a prophy angle attachement that justifies and encourages sanitary practices.

SUMMARY OF THE INVENTION

The present invention addresses these objectives with a disposable prophy angle attachment having as few as four functional components. Each of the functional components is preferably an integral product of an injection molding process and include an elongated tubular housing, a medial drive shaft, a short shaft and a dental implement. Any of the thermoplastic polymers compatible with an injection molding process may be used to form the functional components.

One of the functional components of the invention is an elongated tubular attachment housing having an outer surface that serves as the manual gripping surface for the tool combination. Preferably, the cross-section of the tubular housing is progressively reduced along the tube length from the drive motor coupling end to the spindle head end. The tube length is about 4 inches to about 6 inches. Pursuant to prophy angle utility, the outdrive axis is substantially normal to the length axis of the housing. In close proximity with the spindle head is an assembly facilitation window through the wall shell of the housing tube. The aperture of this assembly window is opened and closed by a latchgate having an integrally molded hinge. The latchgate also includes integrally formed ridges that project into the interior bore space of the housing tube when the latchgate is closed over the window aperture.

At the axial end of the tubular housing opposite from the spindle head, the outside housing surface is shaped and dimensioned for a close slip-fit within an annular space between the outer housing of a dental tool motor and a coaxial alignment tube therein. The outside diameter of the motor plug surface is about 0.5 inches to about 0.6 inches and preferably, about 0.56 inches. Additionally, the outer surface of the prophy angle motor plug includes a circumferential latch groove that cooperates with a latch pawl in the motor housing. When concentrically assembled, a latch pawl barb enters the prophy angle latch groove to prevent undesired axial disassembly. Selectively, the latch pawl barb may rotate out of the latch groove for disassembly.

Another functional component of the prophy angle attachment invention is a medial drive shaft having a quick-coupling hub at one end and a star array of gear teeth in the face plane of the opposite end. The quick-coupling hub has a substantially circular outside surface that is dimensioned to a close slip-fit with the internal bore of a coupling alignment tube element of the tool motor. The medial drive shaft coupling hub also includes receptacles for axially engaged receipt of coupling pins or lugs projecting laterally from the end of a motor shaft.

The geared end of the medial drive shaft is also formed with several journal bearing ridges. A pair of such ridges, for example, are relatively positioned to cooperate with the housing latchgate ridges to secure the axial position of the medial drive shaft when the latchgate is closed without restricting rotational freedom of the medial drive shaft. An annular channel between the bearing ridges provides a lubricant reservoir.

A third functional component of the prophy angle attachment is a short shaft of about 0.375 inches long that fits axially within an approximately 0.32 inch internal bore of the spindle head portion of the tubular housing. An outer end of this short shaft carries a tool spindle to which an appropriate polishing head or brush, for example, is attached. The inner end of the short shaft includes an inside ring array of pinion gear teeth that mesh with the star arrayed gear teeth on the medial drive shaft end. When the short shaft is aligned axially within the spindle head bore and the pinion gear teeth are meshed with the medial drive shaft gear teeth, physical interference between the respective gear support structures prevents axial withdrawl of the short shaft from the spindle head bore.

Hence, the disposable prophy angle attachment of the present invention may be manufactured with such length as to directly couple the spindle head with the tool motor. This manufacture is accomplished with such economy as to be disposable after a single use. Correspondently, the medial drive shaft and the short shaft components of the invention may be assembled with such accuracy as to greatly reduce operational vibration.

BRIEF DESCRIPTION OF THE DRAWINGS

FIG. 1 is a pictorial view of the assembled invention;

FIG. 2 is a partial isometric view of a dental tool motor;

FIG. 3 is a partial cross-section of the invention as viewed along cutting plane 3—3 of FIG. 1;

FIG. 4 is a partial cross-section of the present invention coupling hub;

FIG. 5 is a partial cross-section of the invention as viewed along the cutting plane 5—5 of FIG. 1;

FIG. 6A is a cross-sectional view of the invention as viewed along the cutting plane 6—6 of FIG. 5 and with an open latchgate; and FIG. 6B is a cross-sectional view of the invention as viewed along the cutting plane 6—6 of FIG. 5 and with a closed latchgate.

DESCRIPTION OF THE PREFERRED EMBODIMENTS

In relating the invention description to the drawings, the same reference character is used to identify the same or similar elements of the invention structures throughout the several figures of the drawings. FIG. 1 pictorially illustrates the invention assembly comprising a low speed dental tool motor 10, an air supply conduit 12 and a prophy angle attachment 14. The prophy angle attachment length is preferably about 4 to 6 inches and tapered with an aspect ratio of about 0.016:1 to about 0.055:1. In this instance, an aspect ratio is defined as the change in diameter ($\Delta d$) over a unit of length, e.g. $\Delta d$:1. A polishing implement 16 is shown to be attached to the prophy angle tool spindle. Preferably, the dental tool motor 10 is a Midwest low speed air motor manufactured by Midwest Dental Products of Des Plains, Ill. There are, however, numerous other manufacturers and models of low speed dental motors to which the invention principles may be adapted. Usually, such dental tool motors 10 are air turbine devices that extract the energy from an expanding air flow for rotatively driving a power output shaft 18 such as that shown by FIG. 3. Preferred embodiments of the present invention utilize a selectively engaged coupling means such as lugs or a dowel pin 20 for torque transfer from the motor drive shaft 18 to the coupling hub 22 end of a medial drive shaft 24 within the tapered tubular housing 30 of the attachment 14.

The motor drive shaft 18 is confined to its rotational axis within the motor outdrive housing 40 by a bearing 42. The bearing 42 is set within the internal bore 44 of a coupling alignment tube 46. The alignment tube 46 projects coaxially from a seating collar 48. The seating collar 48 is sized to a contiguous face fit between the collar outside surface and the internal bore surface 41 of the motor outdrive housing 40.

Between the approximately 0.375 inch outside diameter of the coupling alignment tube 46 and the internal bore surface 41 of the motor outdrive housing 40 is an annular space 50. Depth of the annular space 50, about 0.3175 inch, is terminated by an abutment ledge surface 52 on the alignment tube seating collar 48.

An elongated aperture 54 through the wall of the motor outdrive housing 40 provides a flush surface receptacle for a latch pawl 56. A pair of earpieces 58 extending from opposite sides of the latch pawl are secured by a retainer pin 60. The pin 60 passes through the outdrive housing wall 40 and the earpieces 58 to function as a rocker axle for the latch pawl 56. A single leaf spring 62 secured to the internal bore wall 41 of the outdrive housing provides a rotational bias for the latch pawl 56 about the pin 60. Such rotational bias is oriented to urge the latch pawl barb 64 toward the rotational axis of the motor drive shaft 18.

The base end of the prophy angle attachment 14 includes a substantially cylindrically formed coupling plug surface 70 having an outside diameter of about 0.56 inch and a close slip-fit within the internal bore 41 of the motor outdrive housing. The plug surface is terminated by an abutment shoulder 72 extending radially between the outer surface of the prophy angle housing 30 and the smaller diameter plug surface 70. A latching groove 74 circumscribes the plug surface 70 perimeter for receipt of the pawl barb 64.

The tapered length prophy angle attachment 14 is coupled with the motor 10 by insertion of the coupling alignment tube 46, about 0.317 inch, into the internal bore 32 of the prophy angle housing. At full penetration depth of the alignment tube 46, the distal end 76 of the prophy angle housing tube engages the seating collar abutment ledge 52. In this alignment, the barb 64 of the spring biased latching pawl drops into the latching groove 74 thereby preventing extraction of the prophy angle attachment 14 from the motor 10. Although the attachment 14 may not be extracted axially from the motor outdrive housing 40 while the latching pawl barb 64 penetrates the latching grove 74, the attachment 14 is rotationally free about the axis of drive shaft 18. Selective disassembly is accomplished, however, by manually depressing the end of the latching pawl opposite from the barb 64 to rotatively lift the barb out of the latching groove 74.

The medial drive shaft quick-coupling hub 22 comprises a circular journal surface 26 having a close slip-fit dimensional relation to the internal bore surface 44 of the coupling alignment tube 46. At the distal end of the coupling hub 22 is a wedge or funnel mouth coupling receptacle 28. In its most simple form, the hub 22 is given a socket boring 34 along the hub axis. Annular walls between the outer hub surface and the socket are removed in a V-notch pattern 36, for example. The V-notch apex is axially positioned from the hub distal end for receipt of the medial drive shaft coupling pin 20 (lugs) at the point of coincidence between the prophy angle distal end 76 and the abutment ledge 52.

With respect to FIG. 5, the prophy angle housing 30 is reduced to a smaller O.D. cross-section of about 0.375 inch near the outdrive head 80. Similarly, the internal bore 82 of the tubular housing 30 may be correspondingly reduced near the implement drive head to about 0.28 inch. This reduced diameter bore 82 is dimensionally coordinated with three, for example, circular bearing ridges 84, 86 and 88 on the medial drive shaft. These bearing ridges maintain the axial concentricity of the medial drive shaft drive end during rotational engagement with the geared short-shaft 100. The intermediate bearing ridge 86 is axially separated from the inner bearing ridge 84 to provide oppositely facing annular surfaces. An axial confinement channel 90 is thereby formed between these oppositely facing annular surfaces. This channel 90 may be used advantageously as a reservoir for sterile, non-toxic lubricant. A latchgate 92 having a "living" hinge connection 98 to the housing wall 30 includes a pair of thrust curbs 94 and 96. The thrust curbs 94 and 96 are axially separated by a distance that is slightly less than the axial distance between the oppositely facing annular surfaces respective to the bearing ridges 84 and 86.

Referring to FIG. 6A, the latchgate 92 is shown to be opened by rotation about the living hinge 98. In this open position, the thrust curbs 94 and 96 are withdrawn from the internal space of bore 82 thereby permitting the bearing ridges 84, 86 and 88 to pass axially along the bore 82 past the latchgate 92 position. When the latchgate 92 is closed, as shown by FIGS. 5 and 6B, the thrust curbs 94 and 96 penetrate the confinement channel 90 between the bearing ridges 84 and 86 to prevent axial movement of the medial drive shaft 74 in either axial direction.

As described previously, the outer bearing ridge 88 contributes to the necessary medial drive shaft alignment. Additionally, however, the outer bearing ridge 88 provides a facing plate base for structural support of gear teeth in a star array 104. This gear tooth array 104 is confined by the thrust curbs 94 and 96 to rotate about the medial drive shaft axis within a cylindrical space 106 between the pinion gear 108 around the inner end of the short shaft 100 and an annular abutment face 110. The short shaft spindle end 102 is axially confined within the drive head 80 by a journal element 112. The geared end of the short shaft 100 is axially confined by a stationary spindle pin 114 that axially engages a bearing socket 116. Structural interference of the medial drive shaft gears 104 with the pinion gears 108 and abutment face 110 prevents undesired axial extraction of the short shaft 100 after assembly.

Each of the preferred embodiment components may be produced from any suitable plastic or inexpensive synthetic polymeric material. The invention is particularly well adapted to plastic injection mold production. In such case, the prophy angle attachment housing 30, including the implement drive head 80 and the latchgate 92, is finish formed within an injection mold from injected polymer as a singularly integral unit. Similarly, the medial drive shaft 24 is injection molded integrally with the coupling hub 22, the bearing ridges 84, 86 and 88 and the gear teeth 104. The short shaft 100 is a third independent component.

For operational assembly, the short shaft 100 is first inserted full depth into the drive head bore 81. Next, the geared end 104 of the medial drive shaft 24 is inserted axially along the internal bore 32 of the housing 30 with the housing latchgate 92 in the open position as shown by FIG. 6A. The medial drive shaft gear teeth 104 are pushed into meshed engagement with the pinion gear teeth 108. When the teeth of gears 104 and 108 are meshed, the shaft gear array 104 is located within the short shaft cylindrical space 106 thereby preventing axial removal of the short shaft from the drive head bore 81. Simultaneously, the bearing ridges 84 and 86 are axially aligned to flank the thrust curbs 94 and 96 when the latchgate 92 is rotated about the living hinge 98.

A latching lobe surface 99 on the latchgate 92 swinging face is distorted to pass the gate opening. Once the latchgate is closed, the lobe surface 99 bears against the internal bore surface 82 to prevent the latchgate from opening again.

In a non-illustrated embodiment of the invention, the medial drive shaft may also be axially confined by a single thrust curb on the latchgate 92 that is aligned to mesh with a circular slot formed between the bearing ridges 84 and 86.

In summary, the prophy angle attachment of the present invention is an interlocked assemblage of preferably three integrally formed components. The star gear array 104 holds the short shaft 100 in place and the thrust curbs 94 and 96 hold the medial drive shaft 24 in place. Axial alignment of the medial drive shaft coupling end is maintained by the internal bore 44 of the motor coupling alignment tube 46. The external surface of the alignment tube 46 contributes structural and assembly strength to the joint.

The foregoing description of the invention preferred embodiments has been presented for purposes of illustration and description. It is not intended to be exhaustive or to limit the invention to the precise form disclosed. Obvious modifications or variations are possible in light of the above teachings. These embodiments were chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

As my invention, therefore,

I claim:

1. The combination of a dental tool motor and a disposable dental tool attachment: said motor having a rotary power output shaft that is axially confined within a coupling alignment tube, said coupling alignment tube being substantially coaxially secured to a motor housing, an annular space provided between an inside surface of said motor housing and an outside surface of said coupling alignment tube, said power output shaft having selectively disengaged means for transmitting torque to a medial drive shaft; said dental tool attachment having an elongated tubular housing, a medial drive shaft, and a short shaft, said tubular housing having substantially cylindrical first and second internal housing bores proximate of respectively opposite tubular housing ends and an elongated void space between said opposite housing ends, a first of the tubular housing ends adapted to substantially fill said annular space between said motor housing and said coupling alignment tube, said tubular housing further having a drive head at a second end thereof, said drive head having an axial bore aligned substantially transverse of the first and second internal housing bores, said medial drive shaft having a coupling end and a gear face end, said coupling end having axially engaged and disengaged torque transfer surfaces for selective connection with said power output shaft, said coupling end further having bearing surfaces for substantial coaxial confinement of a rotational axis respective to the medial drive shaft coupling end within said motor coupling alignment tube, the medial drive shaft gear face end having journal means for substantial coaxial confinement of a rotational axis within said second internal housing bore, the short shaft of said dental tool attachment having a pinion gear proximate of one end thereof and a dental implement attachment means at an opposite end, said medial drive shaft gear face being disposed for meshed engagement with said pinion gear.

2. The combination described by claim 1 wherein the means for transmitting torque from said motor power output shaft to said a medial drive shaft comprises pin means projecting from substantially laterally opposite sides of said motor power output shaft.

3. The combination described by claim 2 wherein the coupling end of said medial drive shaft comprises a coupling hub, said hub having a partially annular wall around an axial socket, said annular wall having a pair of diametrically opposite notches therein for meshed receipt of said pins means.

4. The combination described by claim 3 wherein an internal bore diameter respective to the axial socket of said coupling hub substantially conforms to an outside diameter respective to said motor power output shaft.

5. The combination described by claim 4 wherein an external diameter respective to said coupling hub substantially conforms to an inside surface diameter of said coupling alignment tube whereby said coupling hub is substantially coaxially confined and rotatable within said coupling alignment tube.

6. A disposable prophy angle attachment comprising:
   A. an elongated tubular housing for rotatively confining a drive shaft that transfers rotational drive power between a motor output shaft and an implement connection shaft, said elongated tubular housing having a tubular wall around an elongated void space, said tubular wall being distally terminated at one end thereof by a drive head and at an opposite end by a motor coupling plug, said coupling plug having means for securing said tubular housing to a motor and selective release therefrom, said drive head having an implement shaft receptacle, a cylindrical axis respective to said implement shaft receptacle being aligned substantially transverse to the length of said tubular housing;
   B. a medial drive shaft having an axial length for traversing the length of said tubular housing void space, torque transfer coupling means at one longitudinal end of said drive shaft and drive shaft gear means at an opposite longitudinal end, said drive shaft having rotational axis alignment means with said coupling means and said gear means for radially confining a rotational axis of said drive shaft; and,
   C. implement connection shaft means having pinion gear teeth at one end thereof and dental implement attachment means at an opposite end thereof.

7. A prophy angle attachment as described by claim 6 wherein said torque transfer coupling means comprises a coupling hub that coaxially sockets a motor output shaft therewith.

8. A prophy angle attachment as described by claim 7 wherein said coupling hub comprises a partially annular wall around a hub socket bore, said annular wall having at least a pair of notches therein for axial receipt of lugs projecting laterally from said motor output shaft.

9. A prophy angle attachment as described by claim 8 wherein an internal diameter respective to said hub socket bore substantially conforms to an outside diameter respective to said motor output shaft.

10. A prophy angle attachment described by claim 9 wherein an external diameter respective to said coupling hub substantially conforms to an internal diameter respective to a coupling alignment tube within a cooperative drive motor.

11. A disposable prophy angle comprising:
   A. an elongated plastic housing for rotatively confining an elongated drive shaft that transfers rotational drive power between a motor output shaft and an implement connection shaft, said elongated housing comprising a tubular wall around an elongated void space, said wall having an outer surface that is tapered with an aspect ratio of about 0.016:1 to about 0.055:1 over a length of about 4 inches to about 6 inches between motor coupling means proximate of one end of the tubular wall and an implement drive head at an opposite end of the tubular wall;
   B. a plastic drive shaft having an axial length for traversing the length of said elongated void space, shaft coupling means at one longitudinal end of said drive shaft for rotational transfer of torque about a first axis from a motor output shaft to gear means at an opposite longitudinal end, said coupling means and gear means having first axis confinement means to restrain radial displacement of said drive shaft; and,
   C. plastic implement shaft means disposed for rotation about a second axis aligned substantially normal to said first axis, said implement shaft means further having implement attachment means at one end thereof and gear teeth meshed with said drive shaft gear means.

12. A disposable prophy angle as described by claim 11 wherein said coupling means comprises a hub having coaxial socket means for receipt of a motor output shaft.

13. A disposable prophy angle as described by claim 12 wherein said hub comprises a partially annular wall around said socket means, said annular wall having at least a pair of notches therein for axial receipt of lugs projecting laterally from said motor output shaft.

14. A disposable prophy angle as described by claim 13 wherein an internal diameter respective to said hub socket means substantially conforms to an outside diameter respective to said motor output shaft.

15. A disposable prophy angle as described by claim 14 wherein an external diameter respective to said annular wall substantially conforms to an internal diameter respective to a coupling alignment tube within a cooperative motor.

* * * * *

UNITED STATES PATENT AND TRADEMARK OFFICE
CERTIFICATE OF CORRECTION

PATENT NO. : 5,911,577
DATED : June 15, 1999
INVENTOR(S) : Steven Ross Henrikson It is certified that error appears in the above-identified patent and that said Letters Patent is hereby corrected as shown below:

Column 1, line 46, after "be" delete "sterized" and replace with --sterilized--.

Column 2, line 9, delete "attachement" and replace with --attachment--.

Column 3, line 13, delete "withdrawl" and replace with --withdrawal--.

Column 3, line 19, delete "Correspondently" and replace with --Correpondingly--.

Signed and Sealed this

First Day of February, 2000

Attest:

Q. TODD DICKINSON

*Attesting Officer*  *Acting Commissioner of Patents and Trademarks*